United States Patent
Weiler et al.

(10) Patent No.: US 10,130,414 B2
(45) Date of Patent: Nov. 20, 2018

(54) SURGICAL INSTRUMENT

(71) Applicant: Erbe Elektromedizin GmbH, Tuebingen (DE)

(72) Inventors: Rolf Weiler, Kusterdingen (DE); Volker Mayer, Tuebingen (DE); Heiko Schall, Nuertingen (DE); Achim Brodbeck, Metzingen (DE); Tobias Amann, Geislingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 52 days.

(21) Appl. No.: 14/749,244

(22) Filed: Jun. 24, 2015

(65) Prior Publication Data
US 2015/0374430 A1 Dec. 31, 2015

(30) Foreign Application Priority Data

Jun. 25, 2014 (EP) ..................................... 14173954

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00196* (2013.01);
(Continued)

(58) Field of Classification Search
CPC .... A61B 2018/00601; A61B 2018/607; A61B 2018/0063; A61B 2018/1455
(Continued)

(56) References Cited

U.S. PATENT DOCUMENTS 3,608,554 A * 9/1971 McGuinness ........ A61B 17/282
   24/518
5,700,261 A * 12/1997 Brinkerhoff ....... A61B 18/1445
   606/205
(Continued)

FOREIGN PATENT DOCUMENTS

CN   101969874 A   2/2011
CN   103813762 A   5/2014
(Continued)

OTHER PUBLICATIONS

Office action in correspondeing Korean application No. 2015-0090515, dated May 20, 2016, 11 pages.
(Continued)

*Primary Examiner* — Linda Dvorak
*Assistant Examiner* — Ryan T Clark
(74) *Attorney, Agent, or Firm* — Fitch, Even, Tabin & Flannery LLP (57) ABSTRACT

A sealing instrument (10) including two branches (15, 16) with sealing jaws (19, 20, 36, 37) acted on by a sealing voltage preferably between 80 and 120 volts. Tissue receptacles (53, 54) are separated from one another by a wall-like extension (24), which at its lower edge carries a cutting electrode (31), are defined between the branches (15, 16). A cutting voltage from 300 to 500 volts is applied between a branch (16) and the cutting electrode. When the branches are closed the grasped tissue is sealed simultaneously between the sealing jaws (19, 36 and 20, 37) and is severed by the cutting electrode (31). Even though the tissue is severed completely; for example after 0.3 to 0.5 seconds and the sealing requires more time, the rolls of tissue grasped in the tissue receptacles (53, 54) act as form-fitting protection of the vessel edges in the tool (12).

15 Claims, 5 Drawing Sheets

(52) U.S. Cl.
CPC ............... *A61B 2018/00601* (2013.01); *A61B 2018/00607* (2013.01); *A61B 2018/1455* (2013.01)

(58) Field of Classification Search
USPC .......................................................... 606/46
See application file for complete search history.

(56) References Cited

U.S. PATENT DOCUMENTS

| | | | |
|---|---|---|---|
| 6,113,598 A | 9/2000 | Baker | |
| 6,736,813 B2* | 5/2004 | Yamauchi | A61B 18/1442 606/37 |
| 8,394,094 B2 | 3/2013 | Edwards et al. | |
| 2002/0115997 A1 | 8/2002 | Truckai | |
| 2004/0049185 A1* | 3/2004 | Latterell | A61B 18/1442 606/48 |
| 2005/0113826 A1 | 5/2005 | Johnson et al. | |
| 2005/0159745 A1 | 7/2005 | Truckai et al. | |
| 2007/0078456 A1 | 4/2007 | Dumbauld et al. | |
| 2009/0234355 A1* | 9/2009 | Edwards | A61B 18/1445 606/51 |
| 2010/0137851 A1 | 6/2010 | Lin et al. | |
| 2010/0137854 A1 | 6/2010 | Hosier | |
| 2010/0274244 A1 | 10/2010 | Heard | |
| 2011/0257680 A1 | 10/2011 | Reschke et al. | |
| 2013/0226177 A1* | 8/2013 | Brandt | A61B 18/1442 606/49 |
| 2014/0058382 A1 | 2/2014 | Yang | |
| 2014/0309635 A1 | 10/2014 | Lutze et al. | |

FOREIGN PATENT DOCUMENTS

| | | |
|---|---|---|
| EP | 1958583 A2 | 8/2008 |
| JP | H1028693 A | 2/1998 |
| JP | 2010253278 A | 11/2010 |
| SU | 1223895 A1 | 4/1986 |
| WO | 00/47124 A1 | 8/2000 |
| WO | 2009112802 A1 | 9/2009 |

OTHER PUBLICATIONS

Office action in corresponding Japanese application No. 2015-127113, dated Jul. 6, 2016, 13 pages.
European Search Report for corresponding EP Application No. EP14173954, dated Nov. 25, 2015, 7 pages.
Notice of Final Rejection in corresponding Korean Application No. 2015-0090515, dated Nov. 11, 2016, 6 pages.
Search Report in corresponding Japanese Application No. 2015-127113, dated Jun. 2, 2016, 23 pages.
Office Action in corresponding Russian Application No. 2015 124 783, dated Aug. 30, 2016, 11 pages.
Notice of Final Rejection in corresponding Korean Application No. 2015-0090515, dated Jan. 19, 2017, 6 pages.
First office action in corresponding Chinese application No. 201510359500.9 dated Apr. 14, 2017, 18 pages.

* cited by examiner

SURGICAL INSTRUMENT

RELATED APPLICATION(S)

This application claims the benefit of European Patent Application No. EP 14173954.0 filed Jun. 25, 2014, the contents of which are incorporated herein by reference as if fully rewritten herein.

TECHNICAL FIELD

The invention relates to a surgical instrument for sealing and separating biological tissue.

BACKGROUND

Sealing instruments of the specified type are used to perform operations on living human or animal patients. They are used to grip and seal tissue under the influence of pressure and current flow and also the resultant heat. In addition such instruments can be used to sever coagulated or sealed tissue.

US 2007/0078456 A1 discloses such an instrument having two movable branches, which are used to grasp hollow vessels. The two branches can be powered, such that the grasped and compressed hollow vessel is heated between the branches and the vessel walls are connected to one another. The vessel, which is closed and thus sealed in this respect, can then be severed in the sealing zone by means of a displaceable blade.

In order to seal the vessel, the two branches of the tool have flat contact surfaces, between which the vessel is sealed. The contact surfaces must have a considerable minimum width in order to seal the vessel reliably. The miniaturisation of such tools is thus subject to limits.

Furthermore, U.S. Pat. No. 6,113,598 A discloses an instrument having two branches, wherein one (the upper) branch has a strip-like protrusion, which fits into a groove in the lower branch, which is delimited by two resilient branch halves.

With such an instrument it is possible to resiliently clamp the vessel ends during coagulation. Here too, however, miniaturisation is subject to limits.

US 2002/0115997 A1 discloses an instrument that is intended in particular for the resection of lung tissue. The instrument has two branches, which can be moved towards one another and away from one another, with electrode structures on both branches. The electrode structures are profiled on either side of a cutting slit, through which a separating element can move, such that grasped tissue is held in a form-fitting manner and is sealed between the branches. Here, both the upper and lower branch on each side of the cutting slit contain a positive and a negative contact in order to produce the widest possible sealing edge on the tissue.

U.S. Pat. No. 8,394,094 discloses a similar electrosurgical instrument, in which the cutting electrode is assigned a spring-mounted abutment.

SUMMARY

The object of the invention is to specify a sealing instrument of which the design allows a miniaturisation of the tool.

The sealing instrument according to the invention for endoscopic, laparoscopic or open surgical application has two branches. The first branch has at least two sealing electrodes, which are preferably electrically interconnected. The second branch also has at least two sealing electrodes, which are preferably electrically interconnected. One of the branches (for example the upper) has a cutting electrode support with a wall- or cutting edge-like extension. The other branch has a corresponding counter bearing for the cutting electrode. Sealing electrodes are mounted at the edges of the two branches in order to produce sealing edges on the biological tissue. Tissue receptacles are formed between the cutting electrode and the sealing jaws. These receptacles preferably have such a volume that the current density occurring there is much lower than between the sealing jaws. Electrical power is passed through the tissue grasped between cutting electrode and the sealing jaws, that is to say the tissue located in the tissue receptacles, but during this process said tissue shrinks to a lesser extent compared with the tissue grasped between the jaws for forming a sealing edge. The tissue forms at least one roll, which, when the branches are closed, reaches behind both the first sealing jaw and the second sealing jaw, approximately in a form-fitting manner. The tissue receptacle and the tissue grasped therein thus act as form-fitting protection for the tissue grasped between the sealing jaws, even when only a very narrow sealing edge and a very delicate tissue bead is formed. The tissue cannot slip from the sealing instrument before the tool is opened.

The tissue receptacles preferably have a rectangular cross-section. The base face and the tissue support face are preferably each flat and preferably each extend from one sealing jaw of a branch to the other sealing jaw of the same branch. The base face and the tissue support face preferably adjoin the respective sealing jaws substantially at right angles.

This concept also opens up the possibility of working with a cutting electrode that is activated at the same time as the sealing electrodes, such that the coagulation process and the cutting process thus start at the same time. The tissue can be severed by the cutting electrode before the sealing between the sealing jaws is complete. The simultaneous action of cutting electrode and sealing jaws on the tissue is not compulsory, but possible. The chronological sequence of cutting and sealing is preferably set by the voltages applied to the cutting electrode and to the sealing jaws. The sealing and separation time can thus be reduced, the working process can be simplified, and the instrument can be electrically powered. For example, a sealing voltage (for example 97 V) between the sealing jaws and a cutting voltage (for examples 437 V) between the sealing jaws and the cutting electrode can be applied simultaneously from a supply circuit. The voltages can be delivered from an autotransformer. The power can be supplied initially with a ramp-like current profile and then with constant voltage. The treatment can additionally be performed in a time-controlled manner. A minimum time of 1.4 s and/or a maximum time of for example 2.8 s can be set. As disconnection criterion in the time window thus set, it can be specified that the power supply will be disconnected when, following the first drop of the tissue resistance, a renewed increase in said tissue resistance is determined, whereby a time tolerance of the power supply, for example of 0.4 s, is implemented where appropriate. In addition, the instrument or feeding apparatus thereof can be provided with an overvoltage and spark detection device. A temporary voltage drop can be provided in order to extinguish identified sparks.

In addition the specified concept is capable of being miniaturised. Due to the form-fitting protection of the vessel ends or tissue ends in the tissue receptacles, the sealing zones can be limited to very narrow, almost line-like strips, without the risk that unsealed tissue edges will escape prematurely from the sealing instrument.

The tissue receptacles, which are formed on either side of the cutting electrode, have a form whereby a particularly good form fit is achieved between tissue and closed instrument. In addition the width of the tissue receptacles is preferably greater than the width of the wall-like extension, which carries the cutting electrode. In addition the width of the tissue receptacles is preferably greater than the width of the sealing jaws. This also contributes to a reliable form fit and to a sufficient reduction of the current density within the tissue located in the receptacle.

The sealing jaws preferably have a cross-sectional contour with rounded transitions. In particular the sealing jaws are rounded towards the tissue receptacles, whereby a current concentration is avoided. Here, these rounded portions are formed such that, besides the lower current concentration, a reliable form fit between tissue and closed branches is possible. The sealing jaws of the two branches preferably define sealing gaps with one another, which together define an obtuse angle. The rounding of the sealing jaws that are arranged closest to the cutting electrode can thus obtain a large rounding radius, whereby the current density is limited precisely here. If the cutting electrode is fastened in the upper branch, the rounding radii of the lower branch, which are arranged in the direction of the tissue receptacles, may have a different value compared with the rounding radii of the upper branch. These radii however preferably have the same value. The rounding radii of the sealing jaws on the branch outer side have greater values than the rounding radii in the direction of the tissue receptacles. The tissue effect outside the branches can thus be better controlled. Due to the inclined position of the sealing gaps, the branches are automatically centred relative to one another. In addition the sealing jaws at the clamping faces thereof have radii in the direction of the tissue receptacles from for example 0.05 mm to 0.1 mm in order to achieve a good form fit between tissue and instrument, and have radii on the branch outer side from for example 0.1 mm to 0.3 mm in order to attain good sealing properties. The clamping faces together define a sealing or clamping gap from 0 to 0.1 mm, preferably 0 to 0.05 mm, which allows secure clamping even of thin tissue.

The sealing jaws may have a main body with insulating regions, for example made of epoxy resin with sealing electrodes arranged in a row, for example made of the material of the main body of the branch, for example high-grade steel. The main body of the branches can be formed from a solid material or from a stamped/bent heart. The electrodes of opposite sealing jaws are preferably arranged or formed in a manner not overlapping one another. The insulating regions can be formed by (cast or injected) inserts inserted or moulded into the branches or by a number of local coatings made of insulating material. Alternatively, a branch can be formed from ceramic, wherein it is then formed so as to be conductive, for example metallised, in the region of the sealing electrodes. It is also possible to form the branch from ceramics having different properties. The branch for example can be formed exclusively from ceramic, wherein it then comprises a non-conductive ceramic substance of the insulating regions and a conductive ceramic substance for the electrode region. The insulating regions prevent an electrical short circuit between the sealing electrodes of the two sealing jaws, even when the branches touch. The mutual longitudinal spacing between electrodes of the two branches is 0.1 mm to 0.3 mm, preferably 0.25 mm. In addition, a current flow is provided in the biological tissue having a component along the sealing jaws, i.e. an extension of the current parts with an improvement of the thermally biological effect. In addition, the sealing jaws on the sides thereof facing the tissue receptacles can be provided with non-metal material, for example PTFE, plastic resin or the like. The current flow of the cutting current is thus concentrated on the one hand to the cutting electrode and on the other hand to the tissue region grasped between the sealing jaws. The risk of the tissue sticking in the tissue receptacles is overcome or considerably minimised.

The cutting electrode support can be formed from ceramic, plastic or an insulation-coated metal. In addition the cutting electrode support may have a surface to which tissue does not adhere. To this end the surface of the cutting electrode support can be formed, for example coated, in an anti-adhesive manner. In addition the cutting electrode support has a high tracking resistance or a high CTI (comparative tracking index) value, preferably above 600. The cutting electrode is preferably embodied as a thin strip, which carries an exposed end face and is anchored via suitable means, in particular a number of feet, in or on the electrode support. The thermal inertia of the cutting electrode is thus limited to a minimum. The counter bearing can be arranged resiliently in order to prevent the tissue from being crushed and in order to guide the cut by electrical influence. This benefits the sealing reliability, since in this way a movement, caused by the tissue cutting, between cutting electrode of one branch and counter bearing of the other branch does not cause a branch movement to the same extent and thus does not cause a movement between opposite sealing jaws. Alternatively or additionally the cutting electrode support can be spring-mounted. In this case the counter bearing can be rigidly fastened.

If the cutting electrode support is formed from plastic the cutting electrode is preferably overmoulded with plastic. The cutting electrode may consist for example of high-grade sheet steel. The width of the cutting electrode is preferably approximately 0.1 mm. The thickness of the plastic on either side of the cutting electrode is preferably approximately 0.15 mm. The cutting electrode preferably terminates/with the two plastic walls covering the flanks of said electrode (no cutting edge protrusion). A thermoset is preferably used as plastic. Alternatively the cutting electrode in the un-used state may protrude slightly beyond the plastic walls, for example by 0.02 mm to 0.04 mm. The protrusion may change during operation of the instrument, for example by burn-up of the cutting electrode support.

If the cutting electrode support is fabricated from ceramic, preferably $ZrO_2$ ceramic, the cutting electrode support and the cutting electrode are prefabricated separately and then joined together. The width of the cutting electrode is preferably 0.2 to 0.25 mm. It may consist of a sheet metal, in particular high-grade sheet steel. The insulating walls on either side of the cutting electrode preferably have a thickness of 0.15 mm. A cutting-edge protrusion from 0.02 mm to 0.04 mm is preferably set. The cutting electrode can be interlocked with the cutting electrode support, jammed therewith or integrally bonded therewith. There is typically a gap between the cutting electrode and the thin insulating walls of the cutting electrode support. This gap can be filled with adhesive, silicone or the like. Alternatively, the cutting electrode may have a lateral insulation, example formed of a paint or a coating, for example parylene. The lateral contact face of the cutting electrode is thus insulated and the influence of a fluid located in the gap between the cutting electrode and cutting electrode support on the cutting effect of the cutting electrode is minimised, preferably prevented.

The counter bearing arranged opposite the cutting electrode may preferably be spring-mounted. The spring travel may be fixed to less than 1 mm, preferably 0.5 mm. The counter bearing is used to maintain the clamping force between the sealing jaws. This is achieved by the mechanical decoupling of the tissue clamping in the region of the sealing jaws from the tissue clamping between cutting electrode and counter bearing. The shrinkages of the tissue during cutting and during sealing are thus also decoupled from the clamping force between the sealing jaws. This effect occurs also in embodiments with rigidly arranged counter bearing and spring-mounted cutting electrode.

The upper side or tissue support face of the counter bearing may sit, when the branches are closed, in another plane compared with the sealing jaws. The cutting plane of the cutting electrode protrudes beyond the sealing jaws of the sealing electrodes arranged on the same branch. The cutting process thus takes place in a different plane compared with the sealing process.

When the branches are open the counter bearing may protrude beyond the sealing jaws of the same branch. When the branches are closed the resilient or resiliently mounted counter bearing is then compressed and in so doing is pressed into the branch. The spring force which works against the cutting element is thus created.

The counter bearing preferably consists of an insulator with anti-adhesive surface, for example made of PTFE, and similar or identical tracking resistance properties as compared with the cutting electrode support. This spring mounting of the counter bearing results in a cutting behaviour with which the cutting gap is adapted to the tissue shrinkage during cutting. The elongate counter bearing may be resilient at the proximal end thereof independently of the distal end thereof and may thus also define a wedge-shaped gap with the cutting electrode when different tissue thicknesses are present along the cutting electrode.

It is, additionally or alternatively, possible to spring mount the cutting element. The counter bearing in this case can be mounted rigidly or likewise resiliently movably. It is also possible to mount one of the elements so as to be pivotable about a transverse axis and to spring mount the other element, for example with particularly small spring travel, for example of less than 0.5 mm, so as to achieve a good adaptation of the cutting electrode and of the counter bearing to different tissue strengths along the cutting electrode.

The method according to the invention for sealing and separating tissue preferably comprises at least the following steps:

Tissue is grasped between two branches such that it is clamped between sealing jaws and also between the cutting electrode and the tissue support face, wherein tissue receptacles are formed between the closed sealing jaws and a cutting electrode support, which tissue receptacles are filled at least in part by parts of the tissue, and energy is fed simultaneously to the sealing jaws and the cutting electrode.

Due to the simultaneous energy feed at the sealing electrodes and the cutting electrode, the processes of sealing vessels and separating (cutting) vessels take place simultaneously. The separation of vessels can be completed before the sealing of the vessels is complete. The tissue receptacles, during the process of vessel sealing, protect the tissue edges within the branches until the sealing process is completely finished. Due to the design according to the invention of the branches in conjunction with the type of energy feed according to the invention the processing, in particular the separation and the sealing of vessels, can be performed with the highest quality. The entire process is short on the whole due to the simultaneous start of sealing and cutting and generally lasts no longer than the sealing alone.

Further details of advantageous embodiment of the invention will emerge from the drawing of the description or claims. In the drawing:

DETAILED DESCRIPTION

Figure 1:
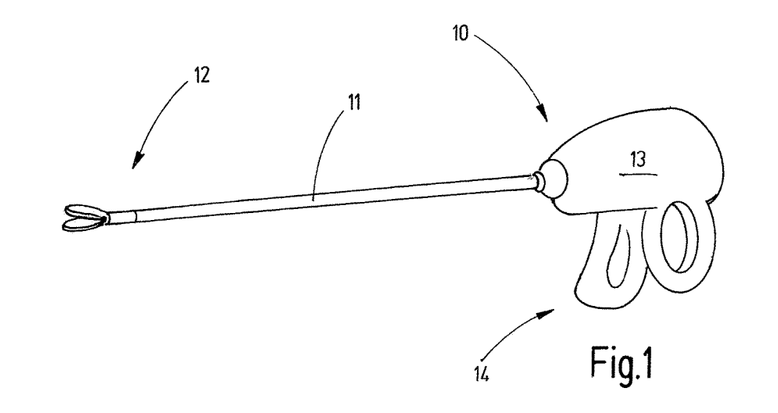
FIG. 1 shows a sealing instrument in schematic perspective overall illustration.

FIG. 1 shows an instrument 10 with an elongate shaft 11, which at the distal end thereof carries a tool 12. The proximal end of the shaft 11 is connected to a housing 13, on which actuation elements 14 for moving and actuating the tool 12 are arranged. The instrument 10 is a sealing instrument. Accordingly, the tool 12 is used to seal and where appropriate sever tissue, wherein vessels and lumen contained in the tissue are to be closed and thus sealed at the tissue edge created.

Figure 2:
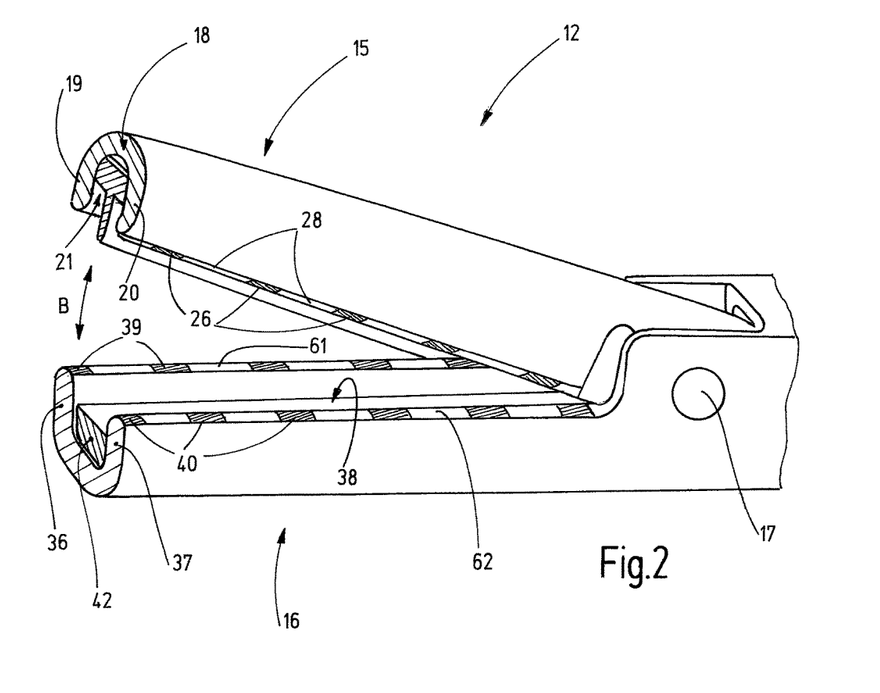
FIG. 2 shows the tool of the sealing instrument according to FIG. 1 in enlarged perspective partially sectional illustration

The tool 12 provided on the instrument 10 is formed in a particular manner. It has a first branch 15, in FIG. 2 the upper branch, and a second branch 16, in FIG. 2 the lower branch, at least one of which is mounted pivotably about a pivot axis 17. Here, depending on the application, the first branch 15 or the second branch 16 or both branches 15, 16 can be mounted so as to be pivotable or otherwise movable about a common or about different pivot axes, such that the branches 15, 16 can be moved towards one another and away from one another.

Figure 3:
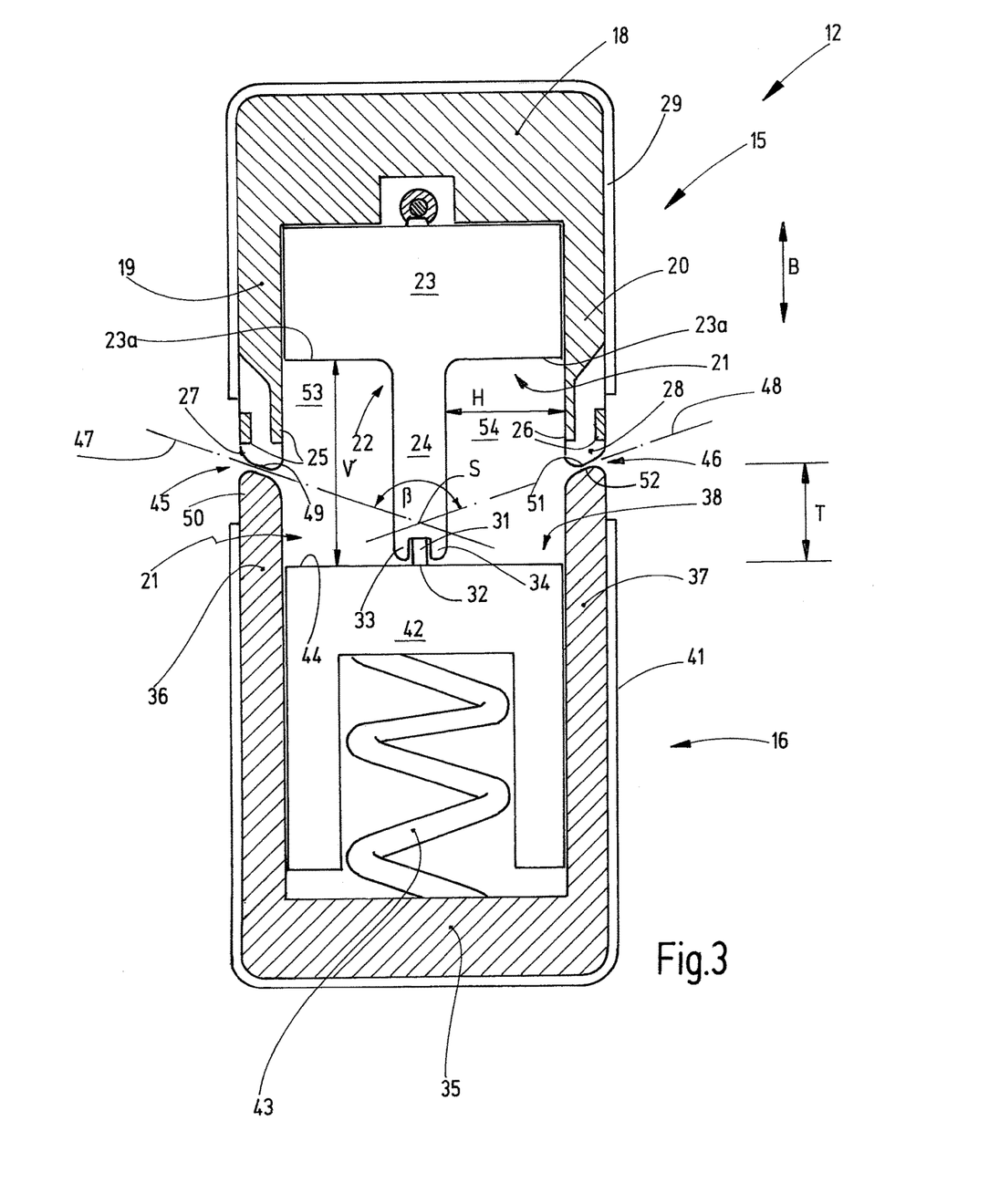
FIG. 3 shows the tool according to FIG. 2 in the closed state in cross section.
Figure 4:
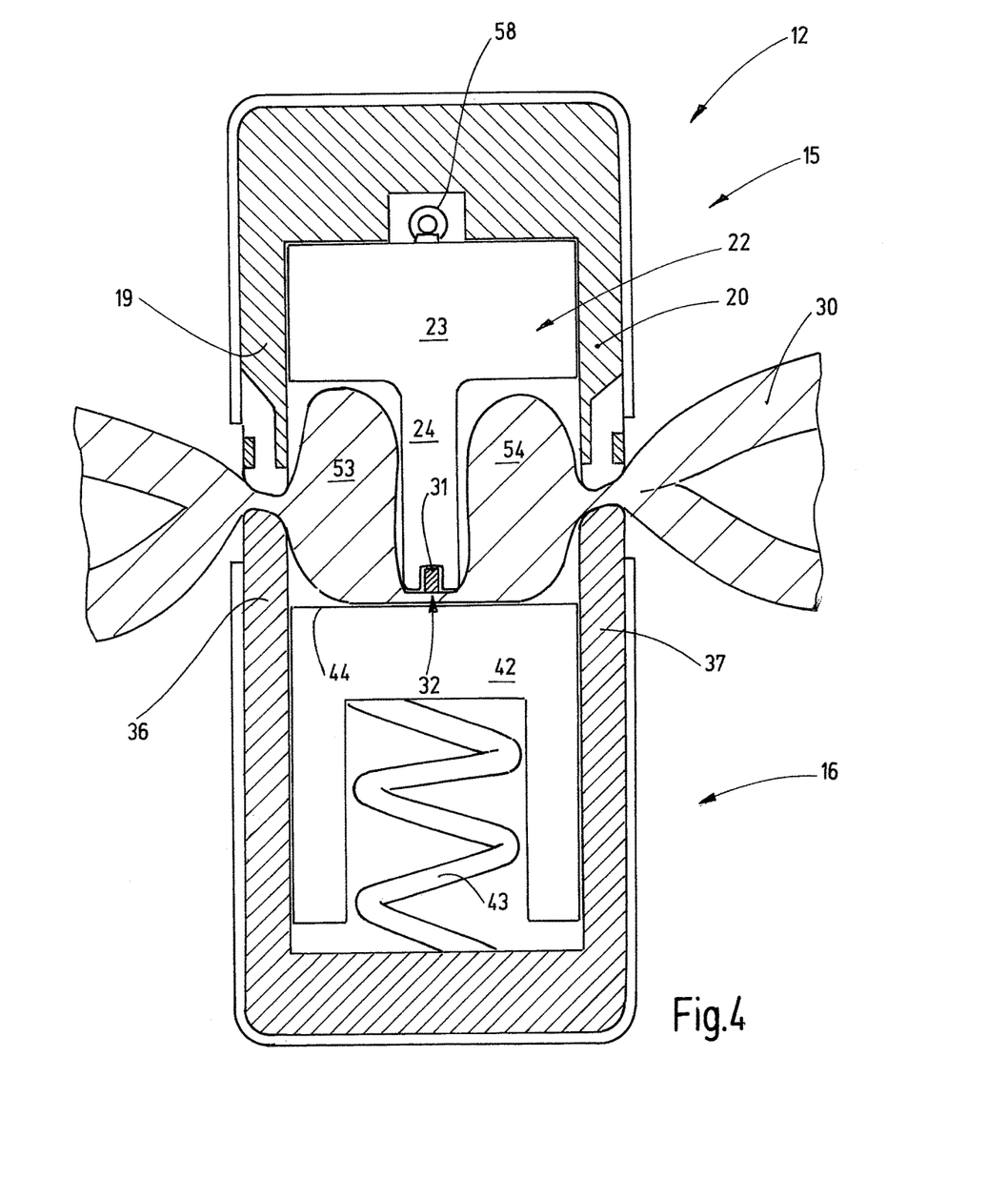
FIG. 4 shows the tool according to FIG. 3 when sealing and separating a hollow vessel.

The branches 15, 16 are illustrated again separately in cross section in FIGS. 3 and 4. The first branch 15 may consist for example of metal or another material resistant to bending. It has a main body 18 with U-profile-shaped cross section. The main body 18 has two first sealing jaws 19, 20, which run parallel to one another, are preferably electrically interconnected, and which delimit a groove 21 between one another. This groove extends preferably over the majority of the length of the first branch 15 and is used to receive a cutting electrode support 22. This has a base 23, which is matched to the contour of the groove 21 and sits therein in a stationary manner, immovably. Starting from a base face 23a, a wall-like extension 24 extends away from the base 23, which for example is rectangular in cross section, preferably centrally between the two sealing jaws 19, 20, such that said extension protrudes from the groove 21. The groove 21 is delimited by the edges of the sealing jaws 19, 20, on which sealing electrodes 25, 26 are formed. The base face 23a, starting from the sealing jaws 19 and 20 respectively, extends as far as the extension 24 and is set back with respect to the sealing electrodes 25, 26. The sealing electrodes 25, 26 can be electrically conductively connected to the main body 18. The sealing electrodes 25, 26, as can be seen in particular from FIG. 2, preferably form a row of conductive individual faces spaced from one another, which are separated from one another by insulating regions 27, 28. The branch 15 may additionally have an electrically insulating coating 29, such that electrical current introduced into the branch 15 can be introduced into biological tissue 30 (FIG. 4) only at the sealing electrodes 25, 26. There is preferably a spacing between the insulating coating 29 and the insulating regions 27, 28, such that the material of the sealing electrodes is not insulated in this region. A good sealing quality is thus achieved.

Figures 5, 6:
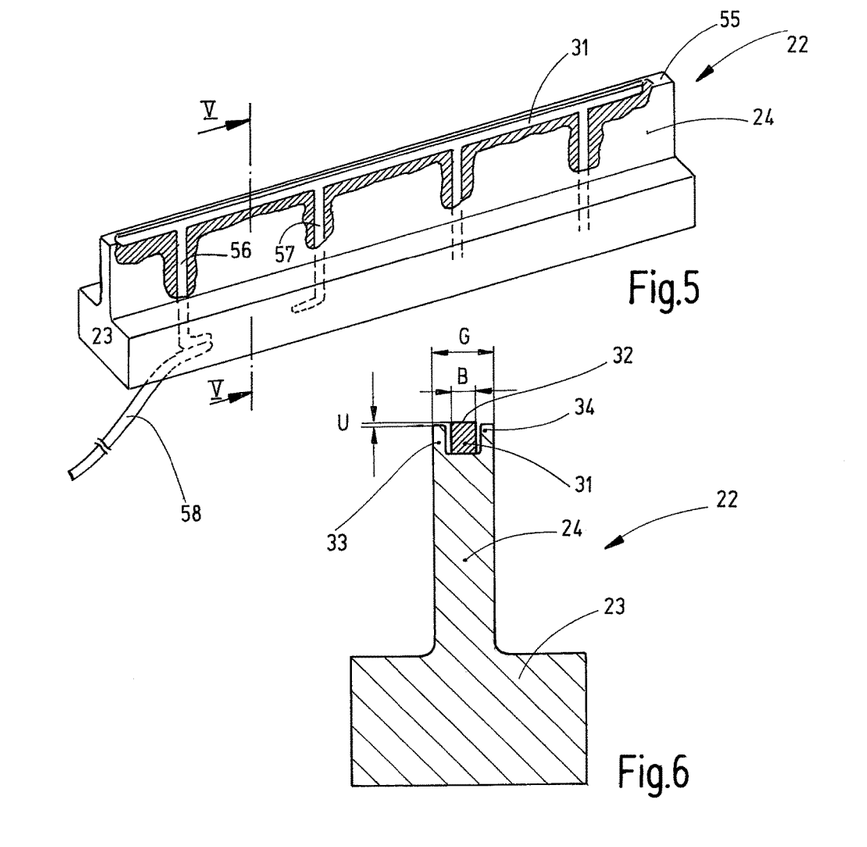
FIG. 5 shows the cutting electrode of the tool according to FIG. 2 in a perspective partly sectional illustration in a first embodiment.
FIG. 6 shows the cutting electrode according to FIG. 5 in cross section.

The cutting electrode support 22 has a cutting electrode 31, which is arranged on the end face of said support. Here, the cutting electrode 31 sits in a groove or recess of the wall-like extension 24, wherein the cutting electrode 31 is exposed via an end face 32. The cutting electrode 31 is received between two groove walls 33, 34. The groove walls 33, 34 preferably have a width that is approximately as large as the width of the cutting electrode 31. Reference is made in this regard to FIG. 6. The width B of the cutting electrode 31 may lie in the range from 0.05 to 0.25 mm and is preferably 0.1 mm. The insulating groove walls 33, 34 preferably have a thickness of the same magnitude. For example, they have a thickness of 0.15 mm. They terminate with one another apart from a small protrusion. The protrusion U of the end face 32 of the cutting electrode 31 beyond the end faces of the groove walls 33, 34 is merely a few tens of μm, for example 0 to 40 μm.

The length of the wall-like extension 24, measured from the base 23 to the cutting electrode 31, is preferably such that the end face 32 protrudes beyond the sealing jaws 19, 20 by for example 0.5 to 1 mm, preferably 0.9 mm accordingly, the tissue support face 44 of the second branch 16 is pressed approximately by the same distance into the second branch 16 by the wall-like extension 24 of the first branch 15 when the branches are closed, in which state the sealing jaws 19, 36 and 20, 37 contact or almost contact one another. This distance is shown in FIG. 3 on the right-hand side beside the tool 12 as dimension T.

FIG. 3 also shows the second branch 16, which likewise has a main body 35 preferably made of electrically conductive material. The main body 35 again has a U-shaped cross section, in which a groove 38 is formed between two second sealing jaws 36, 37. Sealing electrodes 39, 40 (FIG. 2) are again formed on the preferably electrically interconnected second sealing jaws 36, 37 of the second branch 16 and are arranged in a row along the upper edges of the sealing jaws 36, 37. The sealing electrodes 39, 40 are shorter as measured in the jaw longitudinal direction than the insulating regions 27, 28 of the first branch 15. Similarly, the sealing electrodes 25, 26 of the first branch 15 are shorter as measured in the jaw longitudinal direction than the insulating regions 61, 62, that is to say the distances between the second sealing electrodes 39, 40 of the second branch 16. In addition the first sealing electrodes 25, 26 are positioned on the first branch 15 such that they are arranged between the second sealing electrodes 39, 40 when the branches 15, 16 are closed, i.e. they contact the insulating regions 61, 62 of the second branch 16. An electrical short circuit between the first branch 15 and the second branch 16 is thus prevented.

The second branch 16, as shown in FIG. 3, may in turn be provided with an insulating coating 41. A counter bearing 42 for the cutting electrode 31 is arranged in the groove 38. The counter bearing 42 can be mounted movably parallel to the sealing jaws 36, 37 and can be pressed into the groove 38, for example against the force of a spring element 43. The counter bearing 42 for example is a strip-like element, consisting of plastic or ceramic or another electrical non-conductor, preferably with flat tissue support face 44, which forms a support face for the biological tissue 30 and in the rest position is arranged below the sealing electrodes 39, 40, i.e. within the groove 38. The tissue support face 44 extends starting from the sealing jaw 36 to the sealing jaw 37. As necessary the tissue support face 44 can also be formed in a structured manner or in the form of a curve or as a combination thereof.

The spring element 43 may be a compression spring, which is supported at one end at the bottom of the groove 38 and at the other is operatively connected to the counter bearing 42. A plurality of such compression springs may also be arranged along the branch 16 in a row. Alternatively an elastomer element can rest on or be fastened to the bottom of the groove as a spring, on which elastomer element the counter bearing 42 is supported. The spring travel of the counter bearing 42 may be relatively low and for example may be limited to less than a millimeter, preferably 0.5 mm. The spring travel of the counter bearing is dependent on the spring element 43. With a pre-loaded spring element 43, this travel is reduced for example to 0.5 mm or less, and with a non-pre-loaded spring element 43 this travel also includes the path with which the pre-load is generated and may be 1 mm or more. Alternatively the functions of the counter bearing 42 and of the spring element 43 can be provided in a single component, for example a component produced from elastomer.

The sealing jaws 36, 37 are rounded on the upper side thereof. Together with the sealing jaws 19, 20 of the first branch 15, they work in pairs to delimit in each case a gap 45, 46, of which the orientation is indicated in FIG. 3 by dot-and-dash lines 47, 48. The orientation of the gaps 45, 46 can be determined by flat facets 49, 50, 51, 52 provided on the sealing jaws 19, 20, 36, 37. The directions fixed by the gaps 45, 46 and defined by the lines 47, 48 form an obtuse angle with a vertex or point of intersection S, which marks the apex of the angle. This points towards the cutting electrode 31. The obtuse angle preferably lies in a range from 130 to 150°.

The function-determining geometry of the tool 12 additionally includes two tissue receptacles 53, 54. These are formed on either side of the wall-like extension 24 and comprise regions of the grooves 21 and 38. They are delimited vertically between the base 23 and the tissue support face 44 of the counter bearing 42. This vertical extension V is indicated in FIG. 3 and lies, when the branches are closed without tissue, for example in the range from 0.7 mm to 2.5 mm, preferably 1.4 mm. The gap 45, 46 is arranged approximately centrally with respect to the vertical extension V of the tissue receptacle 53 or 54, or preferably is arranged slightly offset towards the base face 23a.

The two tissue receptacles 53, 54 are preferably of equal size. They have a horizontal extension H, which is determined by the distance between the wall-like extension 24 and the respective sealing jaws 19, 36 and 20, 37. This horizontal extension H is preferably much greater than the thickness of the extension 24 to be measured in the same direction. The horizontal extension of one of these tissue receptacles is preferably approximately 0.2 to 0.6 times the vertical extension. When the branches 15, 16 are closed, tissue receptacles 53, 54, which preferably are rectangular in cross section, are formed in the movement direction B between the tissue support face 44 of the counter bearing 42 and the base face 23a of the base 23 and also transversely to the movement direction B between the extension 24 and the first sealing jaws 19, 36 and also between the extension 24 and the second sealing jaws 20, 37.

The instrument described in this regard functions as follows:

In order to seal and separate tissues, in particular hollow vessels or tissues containing hollow vessels, this tissue is grasped between the branches 15, 16. By appropriate actuation of the actuation elements 14, the branches 15, 16 are moved towards one another such that biological tissue 30 is grasped in accordance with FIG. 4. The tissue 30 is subjected during this process to a pressure between the sealing jaws 19, 36 and 20, 37, whereas said tissue is relatively relieved of pressure in the tissue receptacles 53, 54. The cutting electrode 31, however, also exerts a high pressure on the tissue 30.

For tissue sealing an electrical voltage, preferably a high-frequency alternating voltage, is effective between the branches 15, 16, such that an electrical current flows through the biological tissue 30 between the electrodes 25, 26 of the first branch 15 and the electrodes 39, 40 of the second branch 16 so as to heat said tissue and bring about a fusion of the grasped tissue. At the same time, the cutting electrode 31 is activated. This is also fed an electrical voltage, preferably an HF voltage, of which the reference potential lies on one of the branches 15, 16, preferably on the second branch 16, that is to say the sealing electrodes 39, 40.

Due to the small area of the cutting electrode of preferably approximately 1 $mm^2$ to 3 $mm^2$, the current density at the end face 32 is high enough that the biological tissue 30 is quickly severed. The tissue shrinking under the cutting electrode 31 is supported by the resilient counter bearing 42. Said tissue is pressed by the tissue support face 44 towards the end face 32, such that it remains continuously in contact with the cutting electrode 31. The current density, however, decreases drastically already at a short distance from the end face 32. The cross section available for the current flow changes at the side wall of the extension 24 from the narrow gap cross section to the wide cross section of the tissue receptacle 53 or 54. The biological tissue provided there is thus only heated weakly and shrinks to a much lesser extent compared with the tissue beneath the end face 32. Sealing edges thus form between each pairing of the sealing jaws 19, 36 and the sealing jaws 20, 37 respectively, in which sealing edges all lumen in the tissue 30 are closed and a weld seam-like connection is formed in the tissue. At the same time or in a delayed manner the tissue beneath the cutting electrode 31 is severed. Provided the branches 15, 16 closed, the rolls of tissue sitting in the tissue receptacles 53, 54 prevent the tissue 30 from escaping from the tool 12. Only when the tool is opened are the tissue edges released and the treatment process complete.

A key task during the treatment of the tissue 30 is performed by the cutting electrode 31 and the cutting electrode support 22. In order to form the tissue receptacles 53, 54 so as to be as large as possible with minimal overall width of the tool 12, the overall width G (FIG. 6) of the wall-like extension 24 is as small as possible. It is preferably a few tenths of a millimeter in size. This also has the effect that the current density only beneath the cutting electrode 31 has a value sufficient for severing the tissue and then decreases drastically in order to form the rolls sitting in the tissue receptacles 53, 54.

FIG. 5 shows the variant of a cutting electrode 22 made of ceramic. The wall-like extension 24 on the end face thereof has a groove 55, in which the strip-like cutting electrode 31 sits. This preferably has a number of fastening extensions 56, 57, which extend through openings of the cutting electrode support 22. The electrode arrangement thus formed can be adhesively bonded from a cutting electrode support 22 formed with ceramic. One or more fastening extensions 56, 57 can be connected at the base 23 to an electrical line 58, which feeds current to the cutting electrode 31.

The cutting electrode support 22, independently of the specific design thereof, causes a potential isolation between the cutting electrode 31 and the sealing electrodes 25, 26, 39, 40. Whereas the sealing electrodes 39 and 40 used for example as neutral electrodes, the sealing electrodes 25, 26 can be acted on with a voltage causing the sealing, said voltage preferably being lower than the voltage fed to the cutting electrode 31 and intended to sever the tissue. The sealing electrodes 25, 26, 39, 40 preferably have a total electrode area that is greater than ten times, preferably greater than twenty times, the area of the end face 32, such that the energy feed cuts the tissue only at the end face 32, but does not sever the tissue at the sealing electrodes 25, 26, 39, 40.

Figure 7:
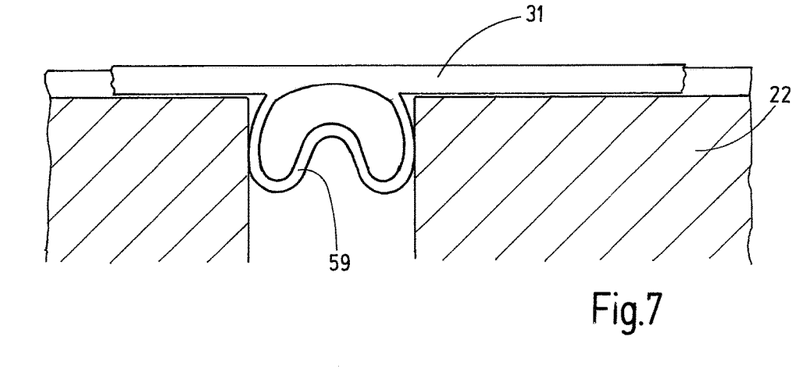
FIG. 7 shows a modified embodiment of a cutting electrode and of a cutting electrode support in longitudinal section.

FIG. 7 illustrates a modified embodiment of the cutting electrode support 22. The cutting electrode 31 again sits in a groove of the cutting electrode support and is anchored there with resilient feet 59. The main body of the cutting electrode support 22 may consist of ceramic or plastic. A thermoset or a silicone which in particular is stable under high-temperature, is flame-retarding and stable against spark erosion, and also has a CTI greater than 600 is suitable as plastic. In addition, it should have sufficiently high mechanical strength and a heat conductivity greater than one W/mK.

Figure 8:
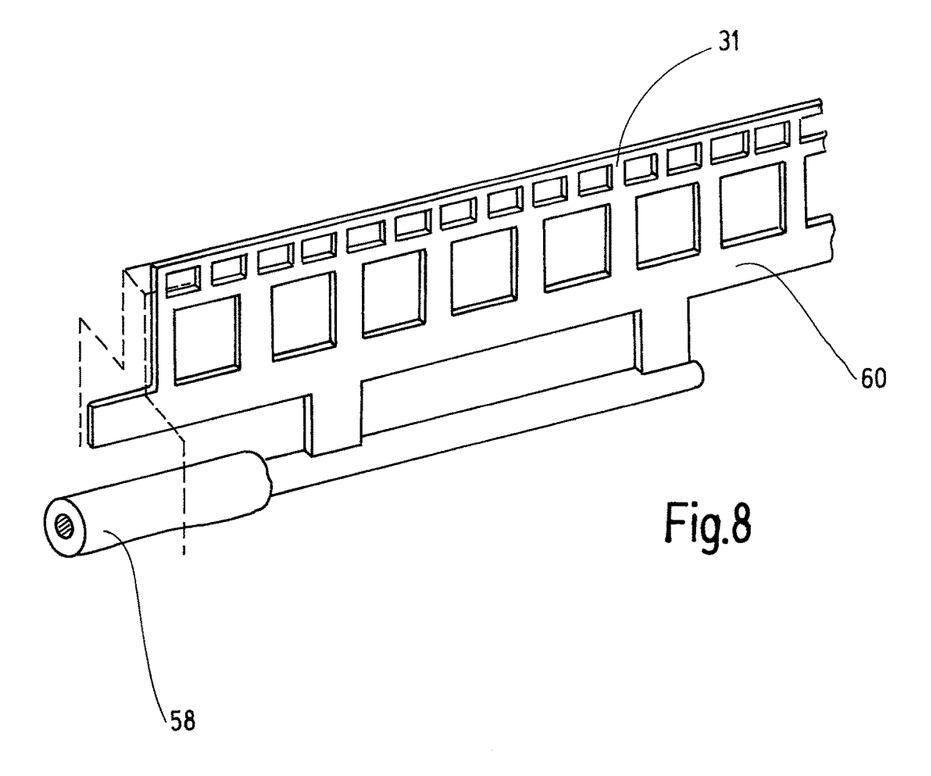
FIG. 8 shows a further modified embodiment of a cutting electrode in perspective illustration.

Such a plastic can be provided in particular with an electrode inlay 60 according to FIG. 8. The cutting electrode 31 here too as in all other embodiments may consist of a sheet metal, for example of high-grade steel. An inner connection of plastic and electrode inlay 60 and also a low heat input into the plastic is achieved by the numerous windows provided in the electrode inlay 60.

A surgical instrument 10 intended in particular for delicate procedures has two branches 15, 16 with sealing jaws 19, 20, 36, 37, which can be acted on with a sealing voltage, preferably between 80 and 120 volts. Tissue receptacles 53, 54, which are separated from one another by a wall-like extension 24, which at its lower edge carries a cutting electrode 31, are defined between the branches 15, 16. A cutting voltage from 300 to 500 volts is applied between a branch 16 and the cutting electrode. When the branches are closed the grasped tissue is sealed simultaneously between the sealing jaws 19, 36 and 20, 37 and is severed by the cutting electrode 31. Even though the tissue is severed completely for example after 0.3 to 0.5 seconds and the sealing requires more time, on the whole approximately 1.5 to 3.5 seconds, vessel separation with closed, sealed vessel ends can be attained. Here, the tissue receptacles 53, 54 act as form-fitting protection of the vessel ends already separated and thus ensure the formation of closed vessel ends with tissue edges in the tool 12. The vessel ends are weaker or are not coagulated compared with the sealing zone and thus form roll-like thickened areas, which prevent the tissue edges from escaping from the instrument when said instrument is closed.

LIST OF REFERENCE SIGNS 10 instrument
11 shaft
12 tool
13 housing
14 fastening elements
15 first branch
16 second branch
17 pivot axis
18 main body of the first branch 15
19, 20 first sealing jaw
21 groove
22 cutting electrode support
23 base of the cutting electrode support
23a base face
24 wall-like extension of the cutting electrode support
25, 26 sealing electrodes of the first branch
27, 28 insulating regions of 15
29 electrically insulating coating
30 biological tissue
31 cutting electrode
32 end face
33, 34 groove walls
B width of the cutting electrode
U protrusion
35 main body
36, 37 second sealing jaw
38 groove
39, 40 sealing electrodes of the second branch
41 insulating coating
42 counter bearing
43 spring element
44 tissue support face
45 gap between the sealing jaws 19 and 36
46 gap between the sealing jaws 20 and 37
47 line illustrating the orientation of the gap 45
48 line illustrating the orientation of the gap 46
49-52 facets
53, 54 tissue receptacles
V vertical extension of the tissue receptacles 53, 54
H horizontal extension of the tissue receptacles 53, 54
55 groove
56, 57 fastening extensions
T protrusion of cutting electrode beyond sealing electrode
58 line
59 feet
60 electrode inlay
61,62 insulating regions of 16

What is claimed is:

1. A surgical instrument (10), comprising:
a first branch (15), which has two first sealing jaws (19, 20) arranged at a distance from one another, which delimit a first groove (21) between one another,
an electrically insulating cutting electrode support (22), which has a base (23), which is arranged in the first groove (21) and which has a base face (23a), which is set back in a movement direction (B) of the first branch so as to be recessed from sealing electrodes (25, 26) arranged on the first sealing jaws (19, 20) and from which a wall-like extension (24) extends away at a distance from the first sealing jaws (19, 20) of the first branch (15), a cutting electrode (31), which is embedded in the cutting electrode support (22) with an end face (32) exposed,
a second branch (16), which has two second sealing jaws (36, 37), which are arranged at a distance from one another and which delimit a second groove (38) between one another,
wherein the first and second branches (15, 16) are movable towards one another and away from one another in the movement direction (B) to be closed and opened,
a counter bearing (42), arranged in the second groove (38), for the cutting electrode (31), wherein the counter bearing (42) has a tissue support face (44), which is set back with respect to sealing electrodes (39, 40) of the second sealing jaws (36, 37) when the branches (15, 16) are closed,
wherein tissue receptacles (53, 54) are formed in the movement direction (B) between the tissue support face (44) of the counter bearing (42) and the base face (23a) of the base (23) and transversely to the movement direction (B) between the extension (24) and each of an opposing pair of the first and second sealing jaws (19, 36) and between the extension (24) and each of another opposing pair of the first and second sealing jaws (20, 37) when the branches (15, 16) are closed;
wherein each tissue receptacle has a width (H) measured transversely to the movement direction (B) between the extension (24) and the first and second sealing jaws (19, 36; 20, 37), and each of the first and second sealing jaws have a width between an inner tissue receptacle facing surface and an opposite outer facing surface thereof measured transversely to the movement direction (B) at tissue contacting surfaces of their respective sealing electrodes (25, 26, 39, 40), wherein the width of each tissue receptacle is greater than said width of each of the first and second sealing jaws.

2. The surgical instrument according to claim 1, wherein the width (H) of the tissue receptacles (53, 54) is smaller than a height measured in the movement direction (B) between the counter bearing (42) and the base (23).

3. The surgical instrument according to claim 1, wherein the width (H) of the tissue receptacles (53, 54) is greater than a thickness of the extension (24) measured in the same direction (24) as the width.

4. The surgical instrument according to claim 1, wherein the first and second sealing jaws (19, 36; 20, 37) terminate at the tissue contacting surfaces that each have a lateral cross-sectional contour with rounded transitions.

5. The surgical instrument according to claim 1, wherein the opposing pairs of the first and second sealing jaws (19, 36; 20, 37) each define a sealing gap (45, 46) therebetween when the branches are closed without the presence of tissue between the opposing pairs of first and second sealing jaws.

6. The surgical instrument according to claim 5, wherein both sealing gaps (45, 46) define an obtuse angle ($\beta$) with respect to one another.

7. The surgical instrument according to claim 6, wherein the obtuse angle ($\beta$) has a vertex (S) that points towards the cutting electrode.

8. The surgical instrument according to claim 1, wherein each sealing jaw (19, 36; 20, 37) has at least one insulating region (27, 28, 61, 62), which is located between the sealing electrodes (25, 26, 39, 40) of each respective sealing jaw arranged in a row.

9. The surgical instrument according to claim 8, wherein the sealing electrodes (25, 26; 39, 40) of each sealing jaw (19, 20; 36, 37) are electrically interconnected.

10. The surgical instrument according to claim 8, wherein the sealing electrodes (25, 26; 39, 40) of the opposing pairs of the first and second sealing jaws (19, 36;20, 37) are arranged in a manner not overlapping one another.

11. The surgical instrument according to claim 1, wherein the cutting electrode support (22) comprises ceramic or plastic.

12. The surgical instrument according to claim 1, wherein the cutting electrode (31) comprises a continuous strip supporting the exposed end face (32), and the strip is anchored in the electrode support (22) via a plurality of fastening extensions (56, 57).

13. The surgical instrument according to claim 1, wherein the cutting electrode (31) comprises a continuous strip supporting the exposed end face (32), and the strip is anchored in the electrode support (22) via a plurality of resilient feet (59).

14. The surgical instrument according to claim 1, wherein the cutting electrode support (22) is rigidly disposed in the first groove (21) and the counter bearing (42) is movably disposed in the second groove (38), or wherein the cutting electrode support (22) is movably disposed in the first groove (21) and the counter bearing (42) is rigidly or movably disposed in the second groove (38).

15. A surgical instrument (10), comprising:
- a first branch (15), which has two first sealing jaws (19, 20) arranged at a distance from one another, which delimit a first groove (21) between one another,
- an electrically insulating cutting electrode support (22), which has a base (23), which is arranged in the first groove (21) and which has a base face (23a), which is recessed from sealing electrodes (25, 26) arranged on the first sealing jaws (19, 20) and from which a wall-like extension (24) extends away at a distance from the first sealing jaws (19, 20) of the first branch (15),
- a cutting electrode (31), which is embedded in the cutting electrode support (22) with an end face (32) exposed,
- a second branch (16), which has two second sealing jaws (36, 37), which are arranged at a distance from one another and which delimit a second groove (38) between one another,
- wherein the first and second branches (15, 16) are movable towards one another and away from one another in a movement direction (B) to be closed and opened,
- a counter bearing (42), arranged in the second groove (38), for the cutting electrode (31), wherein the counter bearing (42) has a tissue support face (44), which is set back with respect to sealing electrodes 39, 40 of the second sealing jaws (36, 37) when the branches (15, 16) are closed,
- wherein tissue receptacles (53, 54) are formed in the movement direction (B) between the tissue support face (44) of the counter bearing (42) and the base face (23a) of the base (23) and transversely to the movement direction (B) between the extension (24) and each of an opposing pair of the first and second sealing jaws (19, 36) and between the extension (24) and each of another opposing pair of the first and second sealing jaws (20, 37) when the branches (15, 16) are closed,
- wherein each tissue receptacle has a width (H) measured transversely to the movement direction (B) between the extension (24) and the first and second sealing jaws (19, 36; 20, 37), and each of the first and second sealing jaws have a width between an inner tissue receptacle facing surface and an opposite outer facing surface thereof measured transversely to the movement direction (B) at tissue contacting surfaces of their respective sealing electrodes (25, 26, 39, 40), wherein the width of each tissue receptacle is greater than said width of each of the first and second sealing jaws, and
- wherein the tissue contacting surfaces are rounded towards the tissue receptacles.

\* \* \* \* \*